US012605559B1

(12) United States Patent
Felix et al.

(10) Patent No.: US 12,605,559 B1
(45) Date of Patent: Apr. 21, 2026

(54) DEFIBRILLATOR WITH SOLID STATE PROTECTION CIRCUITRY

(71) Applicant: Bardy Technologies, Inc., Vashon, WA (US)

(72) Inventors: Jason Felix, Vashon Island, WA (US); Gust H. Bardy, Carnation, WA (US)

(73) Assignee: Bardy Technologies, Inc., Bellevue, WA (US)

( * ) Notice: Subject to any disclaimer, the term of this patent is extended or adjusted under 35 U.S.C. 154(b) by 0 days.

(21) Appl. No.: 19/054,893

(22) Filed: Feb. 16, 2025

(51) Int. Cl.
*A61N 1/39* (2006.01)

(52) U.S. Cl.
CPC ....... *A61N 1/39046* (2017.08); *A61N 1/3937* (2013.01); *A61N 1/3981* (2013.01)

(58) Field of Classification Search
None
See application file for complete search history.

(56) References Cited

U.S. PATENT DOCUMENTS

| | | | |
|---|---|---|---|
| 5,713,925 A | 2/1998 | Sullivan | |
| 5,876,424 A | 3/1999 | O'phelan | |
| 6,208,896 B1 | 3/2001 | Mulhauser | |
| 6,377,848 B1 | 4/2002 | Garde et al. | |
| 6,556,864 B1 | 4/2003 | Picardo | |
| 7,848,804 B1 * | 12/2010 | Kroll .................... | A61N 1/3937 607/2 |
| 9,789,326 B2 | 10/2017 | Schwibner | |
| 10,449,380 B2 | 10/2019 | Andrews et al. | |

| | | |
|---|---|---|
| 10,543,376 B2 | 1/2020 | Beyer et al. |
| 10,668,296 B2 | 6/2020 | Meir |
| 10,773,091 B2 | 9/2020 | Andrews et al. |
| 11,077,311 B2 | 8/2021 | Beyer et al. |
| 11,097,121 B2 | 8/2021 | Beyer et al. |
| 11,305,128 B1 | 4/2022 | Beyer et al. |
| 11,318,322 B2 | 5/2022 | Beyer et al. |
| 11,794,026 B1 | 10/2023 | Bardy et al. |

(Continued)

FOREIGN PATENT DOCUMENTS

WO          2022165179          8/2022

OTHER PUBLICATIONS https://web.archive.org/web/20250214112835/https://en.wikipedia.org/wiki/Relay (cached on Feb. 14, 2025).

(Continued)

*Primary Examiner* — Erica S Lee
(74) *Attorney, Agent, or Firm* — Leonid Kisselev

(57) ABSTRACT

AED patient protection circuitry is improved by using triode for alternating current (TRIACs), which are significantly smaller and cheaper than relays. The TRIACs are positioned between a defibrillation waveform generator and the pads through which defibrillation waveforms are delivered to the patient and alternate under the control of a processing element such as a microcontroller between a conductive state in which they allow the defibrillation waveforms to reach the patient through the pads and an isolated state in which they prevent the defibrillation waveforms from reaching the patient through the pads. A voltage monitor interfaced to the microcontroller can monitor current leakage from the TRIACs or other portions of the defibrillator, thus detecting degradation of patient protection circuitry and further increasing defibrillator safety and reliability.

18 Claims, 6 Drawing Sheets

88

(56)  References Cited

U.S. PATENT DOCUMENTS

| | | | |
|---|---|---|---|
| 2002/0133197 A1 | 9/2002 | Snyder et al. | |
| 2004/0002736 A1 | 1/2004 | Waltman | |
| 2004/0044371 A1 | 3/2004 | Tamura et al. | |
| 2004/0068301 A1 | 4/2004 | Waltman et al. | |
| 2004/0143297 A1 | 7/2004 | Ramsey, III | |
| 2006/0111748 A1 | 5/2006 | Bucher | |
| 2009/0156957 A1* | 6/2009 | Linder | A61N 1/3925 |
| | | | 600/547 |
| 2009/0157132 A1 | 6/2009 | Linder et al. | |
| 2011/0202101 A1 | 8/2011 | Tan et al. | |
| 2013/0053911 A1* | 2/2013 | Hareland | A61N 1/3918 |
| | | | 607/6 |
| 2018/0140859 A1 | 5/2018 | Meir | |
| 2018/0161587 A1 | 6/2018 | Beyer et al. | |
| 2019/0044362 A1 | 2/2019 | Beyer et al. | |
| 2019/0117989 A1 | 4/2019 | Andrews et al. | |
| 2020/0094044 A1 | 3/2020 | Andrews et al. | |
| 2020/0254246 A1 | 8/2020 | Zorman et al. | |
| 2021/0093877 A1 | 4/2021 | Beyer et al. | |
| 2021/0257849 A1* | 8/2021 | Keil | H02J 50/10 |
| 2021/0379393 A1 | 12/2021 | Butler | |

OTHER PUBLICATIONS

BTA408X-1000C0T 3Q Triac Product data sheet, retrieved from https://www.ween-semi.com/sites/default/files/2021-11/BTA408X-1000C0T.pdf (Revised May 18, 2020).

6-Pin DIP Random-Phase Triac Driver Output Optocoupler (250/400 V Peak) MOC3010M, MOC3011M, MOC3012M, MOC3020M, MOC3021M, MOC3022M, MOC3023M data sheet, retrieved from https://www.onsemi.com/download/data-sheet/pdf/moc3023m-d.pdf (2016).

HeartSine® samaritan® PAD 350P/360P AEDs Semi-automatic/fully automatic public access defibrillators, "Compact, easy-to-use, lifesaving technology for public access" H009-032-340-AE_350P_360P_Data_ENUS_0521_web-3. Date of Issue May 2021.

HeartSine® samaritan® PAD 350P/360P Connected AEDs Semi-automatic/fully automatic public access defibrillators with integrated Wi-Fi® connectivity; "Readiness matters," H009-043-010-AD_Connected_350P_360P_Data_ENUS_0521_web. Date of Issue May 2021.

Defibtech Lifeline ECG Semi-Automatic Defibrillator with ECG Display Technical Specifications†, DAC-A2702EN-BC Issued: Jan. 15, 2021. Defibtech, LLC • Guilford, CT 06437 USA • 1-203-453-4507 • 1-866-DEFIB-4U (1-866-333-4248) www.defibtech.com.

* cited by examiner

70

88

170

Fig. 5
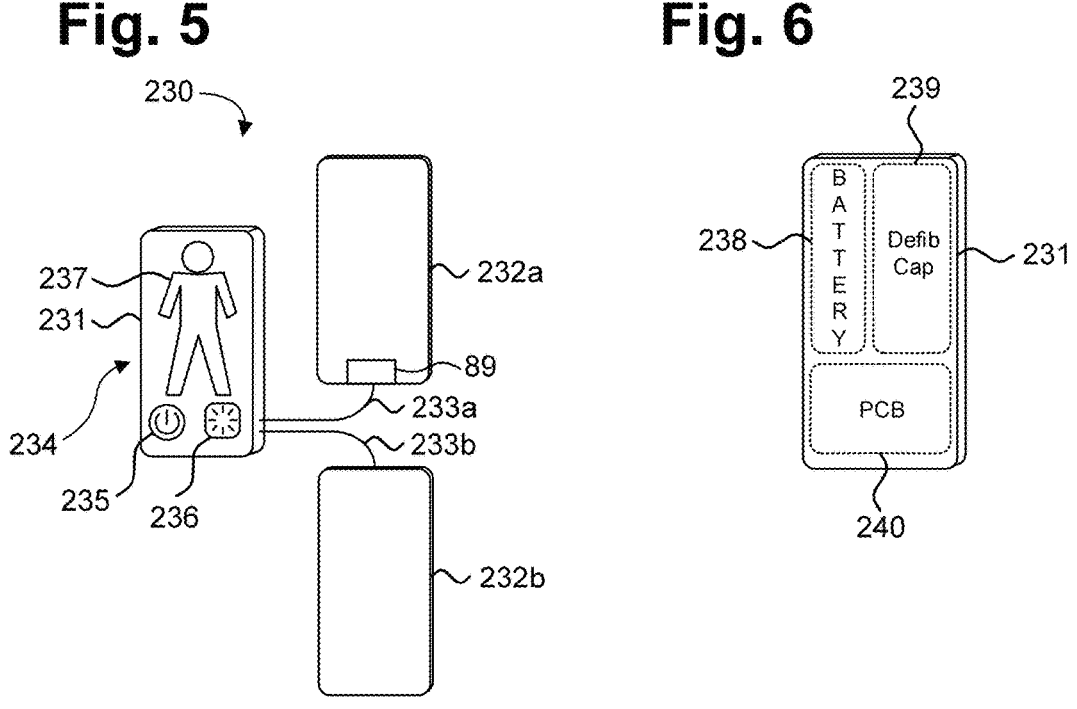
Fig. 6
Fig. 7
Fig. 8
Fig. 9
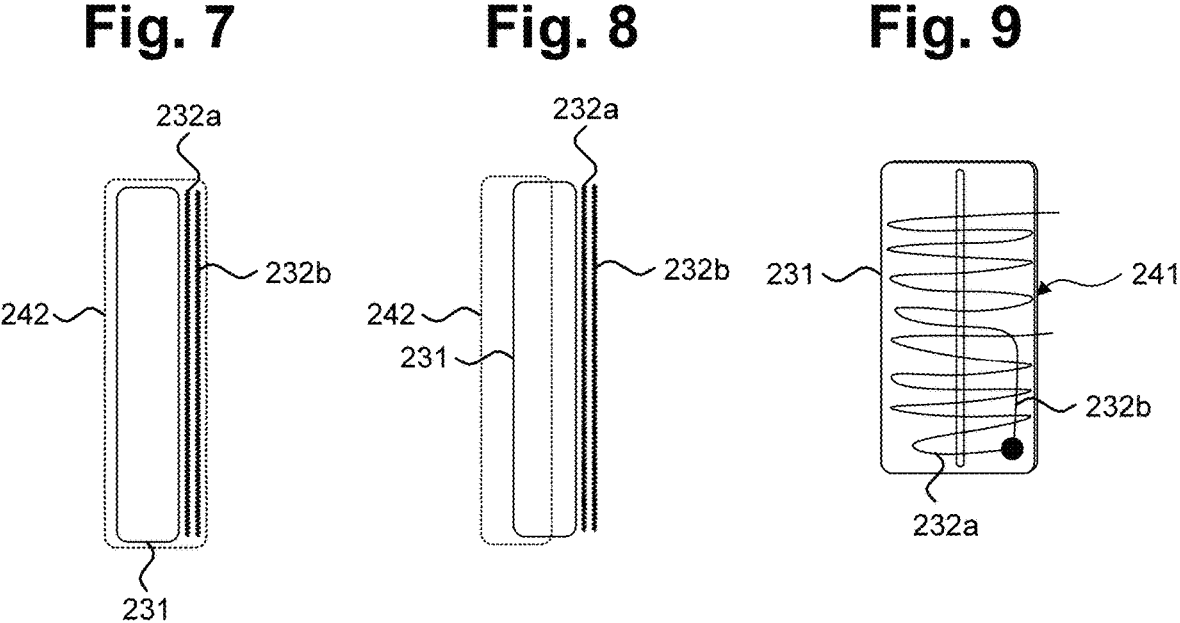

Fig. 10
Fig. 11
Fig. 12
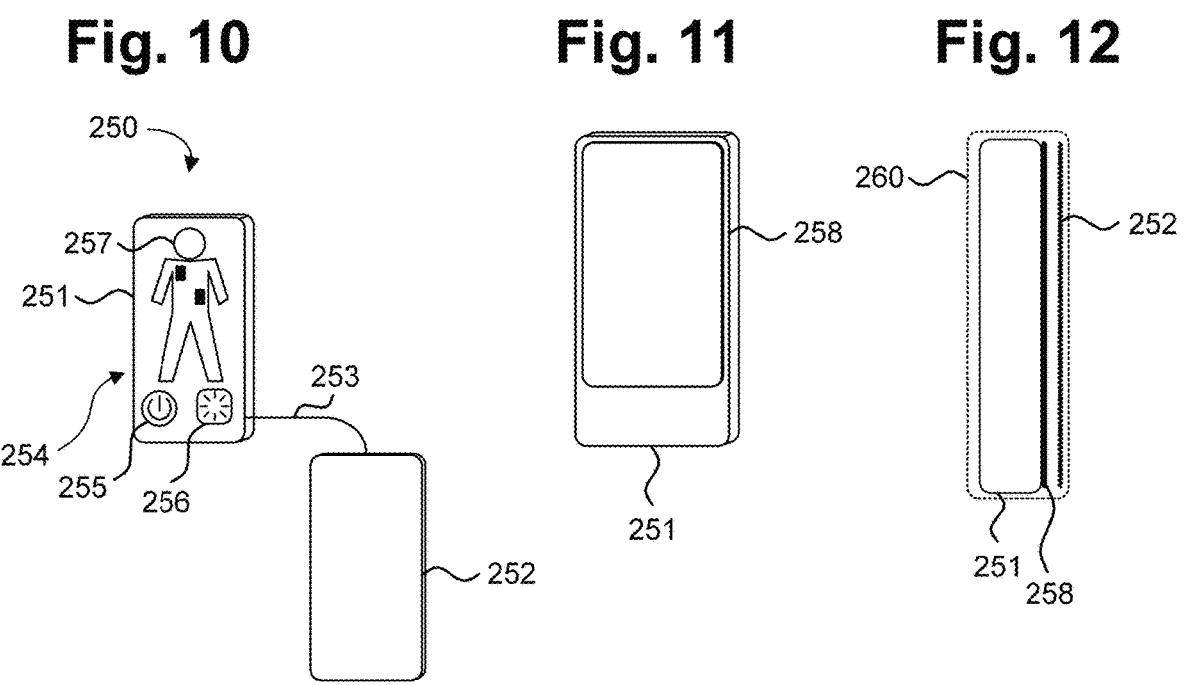
Fig. 13
Fig. 14
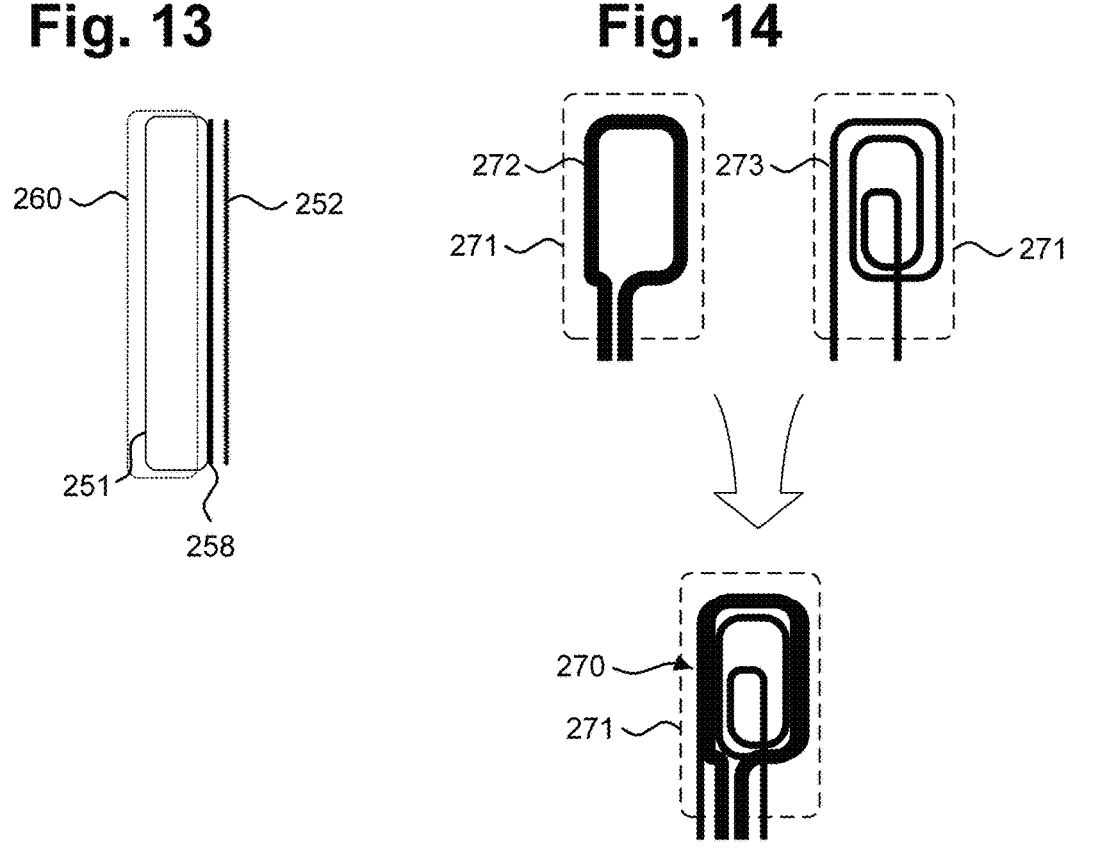

DEFIBRILLATOR WITH SOLID STATE PROTECTION CIRCUITRY

FIELD

This invention relates in general, to defibrillators, and in particular, to a defibrillator with solid state protection circuitry.

BACKGROUND

Sudden cardiac arrest (SCA) is a significant cause of mortality throughout the world and remains a major public health concern causing about 300,000 to 450,000 deaths each year in the United States alone, despite the broad scale teaching of cardiopulmonary resuscitation (CPR) and the implementation of public access automated external defibrillators (AED) in hospitals, ambulances and other public locations, like airports and stadiums. More than 9 of 10 SCA victims still die, even in locales with advanced medic response systems. In most rural locations, the death rate approaches 100%.

SCA occurs when the heart suddenly and unexpectedly stops pumping blood, most commonly caused by a chaotic cardiac rhythm disorder known as ventricular fibrillation (VF). VF is a lethal heart rhythm abnormality that causes the ventricles of the heart to quiver ineffectively, resulting in a failure to pump blood. Accordingly, blood pressure plummets and blood delivery to the brain and all bodily organs essential ceases in 5-10 seconds. SCA from VF constitutes the most time-critical emergency in medicine and is universally lethal within 10-20 minutes without prompt medical attention, specifically the delivery of a high-voltage, high-energy shock across the chest via a defibrillator, the only method known to stop VF. Preferably such a shock is delivered within 5 minutes of the onset of VF. AEDs have the primary function of detecting a shockable rhythm and then delivering the high-voltage shock in a timely manner. The sooner this shock is delivered, the higher the likelihood of survival. Seconds matter. Consequently, ensuring that people have immediate access to an AED is absolutely essential to saving lives from cardiac arrest, where every minute counts.

AEDs have been made publicly available, however, this widespread availability has not meaningfully addressed the problem of SCA. By various accounts, there are approximately 3.2 to 4.5 million AEDs currently deployed in public places in the United States, yet an estimated more than 30 million AEDs are needed to provide sufficient coverage to meaningfully improve cardiac arrest survival rate nationally. Moreover, despite this disparity between the number of devices versus the estimated need, increasing the number of public access AEDs by an order of magnitude would be neither practical in terms of cost or execution nor would such an increase address the problem that SCAs primarily occur in places other than where public access AEDs are found. More than 70% of VF cases occur in or near the home or during routine activities of daily living, like yard-work and gardening, driving, personal recreation, and so on, locations where public access AEDs are not usually found. Immediate employment of an AED from time of victim collapse to shock delivery is optimal for survival, yet public access AEDs are rarely deployed or used in locations where SCAs typically happen and, if they are, their use often comes far too late. Thus, the problem of resuscitating victims from VF is inexorably linked to time and proximity to an AED, which are, in turn, inexorably linked to convenience of use, which is a direct consequence of AED cost, size and weight. Accordingly, to make a positive impact of survivability requires a different approach to AED deployment. One solution would be to provide AED devices that are pocket-sized and modest in weight and cost, so that AEDs become practically ubiquitous, similar to a mobile phone.

The high cost and bulk of conventional public access AEDs are mainly due to the design choices of reusability, elimination of all possible failure modes, and telemetry functionality intended to constantly perform and transmit multi-use readiness checks. These typical AEDs perform self-testing constantly, which depletes the battery, and causes wear on the critical components, requiring large and complex circuit designs and components that will survive constant testing and the resulting high voltage bias that is induced. Several AED product recalls have shown this practice to prematurely degrade components, resulting in an AED becoming non-functional when needed. AEDs are typically designed to eliminate failure modes, which, paradoxically, results in large and complex custom components that are expensive and prone to failure. For example, conventional public access AED capacitors are often rated for use at temperatures of 90° C. and 20,000 discharges back-to-back, conditions that do not remotely resemble the typical use case under any conceivable scenario. Moreover, reusability requirements mean that the batteries must be able to store enough energy to defibrillate multiple patients, perform simulated use testing, as well as have a circuit able to sense when there is not enough energy to be "rescue ready" far in the future.

These are key factors that effectively restrict deployment of public access AEDs only to healthcare providers, first responders, and public areas that are legally required to have an AED, all of which make existing AEDs relatively unavailable and of no use for the majority of VF emergencies that occur at or near the home away from public access AEDs. Moreover, public access AEDs are packaged in large carrying cases weighing several pounds that are too bulky to be convenient for ubiquitous use by the public. Furthermore, excluding costs of the perennial replacement of batteries and pads, AEDs typically cost at purchase between $1200 to $3500, which is too expensive for the average person to buy or to serve as an accessory to accompany activities of daily living.

Further, in addition to the bulkiness of the current AEDs and their carrying cases, other components of public access AEDs further limit how small the AED can be made. All defibrillators manufactured today provide at least three means of patient protection to avoid inadvertent leakage currents and shocks to the patient and personnel who may come in contact with the device. One of these means of protection is always a relay. Relays that can isolate 2 KV and conduct a defibrillation pulse must be quite large and are also expensive. Further, these relays are also prone to damage during application of a parylene coating that happens during manufacture of most defibrillators. Additionally, such relays will violently self-destruct if commutated during the defibrillation pulse.

Therefore, a need remains for providing a new circuit design used for patient protection that in turn facilitates the design of low cost and convenient pocket-sized AEDs. Such a design will also decrease the cost and bulk of conventional AEDs and defibrillation circuits in general, be they external or internal defibrillators.

SUMMARY

AED patient protection circuitry is improved by using one or more triodes for alternating current (TRIACs), which are significantly smaller and cheaper than relays. The TRIACs are positioned between a defibrillation waveform generator and the pads through which defibrillation waveforms are delivered to the patient. During activation under the control of a processing element such as a microcontroller they conduct the defibrillation pulse. When deactivated they provide a means of protection similar to a relay. For an added degree of protection, a voltage monitor interfaced to the microcontroller can monitor current leakage from the TRIACs or other portions of the defibrillator, thus detecting degradation of patient protection circuitry and further increasing defibrillator safety and reliability.

In one embodiment, a defibrillator with solid state patient protection circuitry is provided. The defibrillator includes a therapeutic defibrillation waveform generator configured to generate one or more therapeutic defibrillation waveforms for delivery to a patient via a pair of leads; one or more triodes for alternating current (TRIACs) positioned in series between the therapeutic defibrillation waveform generator and at least one of the leads, each of the TRIACs configured to switch between an enabled, conductive state and an isolated disabled state. The TRIACs will prevent the therapeutic defibrillation waveforms from reaching the patient in the isolated state and allow the defibrillation waveforms to reach the patient in the conductive state. The defibrillator further includes a control element configured to control the therapeutic defibrillation waveform generation by the therapeutic defibrillation waveform generator and the switching of the TRIACs between the conductive state and the isolated state.

In a further embodiment, a defibrillator with patient protection circuitry is provided. The defibrillator includes a therapeutic defibrillation waveform generator configured to generate one or more therapeutic defibrillation waveforms for delivery to a patient via a pair of leads; a charging circuit configured to charge the therapeutic defibrillation waveform generator via a defibrillation capacitor; one or more triodes for alternating current (TRIACs) positioned between the therapeutic defibrillation waveform generator and at least one of the leads, each of the TRIACs configured to switch between a conductive state and an isolated state, wherein the TRIACs prevent the therapeutic defibrillation waveforms from reaching the patient in the isolated state and allow the defibrillation waveforms to reach the patient in the conductive state; and a microcontroller control element configured to deliver one or more of the therapeutic defibrillation waveforms and causes shifting of the TRIACs from the isolated state to the conductive state and activation of the charging circuit and the therapeutic defibrillation waveform generator, wherein the charging circuit and the therapeutic defibrillation waveform generator are not under bias until the activation of the charging circuit.

If significantly reducing the number of deaths from SCA due to VF is to be meaningfully addressed, which has been acknowledged as a problem for over 40 years, the design of conventional AEDs must change to lower cost and decrease size and weight, so that AEDs can be ubiquitously made available, including in every home and every car, as well as in many pockets and purses. Thus, by employing the described patient protection circuitry, the size and reliability of an AED can be meaningfully affected, therefore likely yielding an increased survival rate from cardiac arrest by virtue of its ease of availability because of its pocketability and its lower cost that allows large segments of the population to afford its purchase. This technology may also benefit size and cost reductions for wearable and implantable defibrillators as well as fully functional hospital-based defibrillators.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 5 is a front view showing a disposable single use pocketable AED with dual free-floating electrodes in accordance with one embodiment.

FIG. 6 is a cut-away view showing block component groups contained within the disposable single use pocketable AED of FIG. 5.

FIG. 7 is a side view showing the disposable single use pocketable AED of FIG. 5 with the housing and dual free-floating electrodes stowed in a carrying case.

FIG. 8 is a side view showing the disposable single use pocketable AED of FIG. 5 with the housing and dual free-floating electrodes partially deployed from the carrying case.

FIG. 9 is a back view showing the cable management system of the disposable single use pocketable AED of FIG. 5.

FIG. 10 is a front view showing a disposable single use pocketable AED with a single free-floating electrode in accordance with one embodiment.

FIG. 11 is a rear view showing the integrated electrode of the disposable single use pocketable AED of FIG. 10.

FIG. 12 is a side view showing the disposable single use pocketable AED of FIG. 5 with the housing and single free-floating electrode stowed in a carrying case.

FIG. 13 is a side view showing the disposable single use pocketable AED of FIG. 5 with the housing and single free-floating electrodes partially deployed from the carrying case.

FIG. 14 is a top view diagram showing an electrode pad assembly for use in the disposable single use pocketable AEDs of FIGS. 5 and 10.

DETAILED DESCRIPTION

Figure 1:
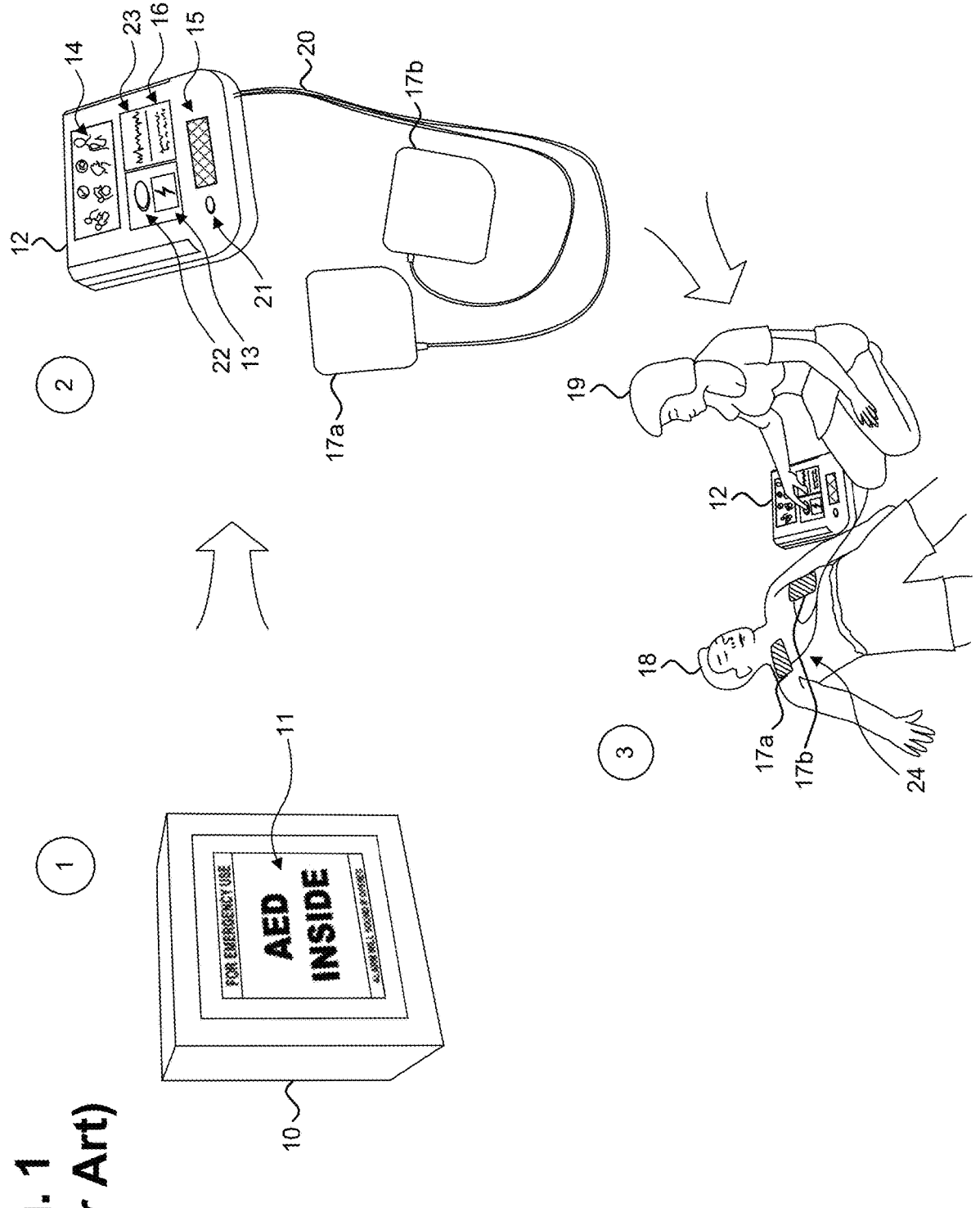
FIG. 1 is a process flow diagram showing, by way of example, a typical prior art use of a public access AED in an SCA situation.

There has been a push to deploy public access AEDs in busy often-frequented places, such as airports, restaurants, casinos, shopping centers, and stadiums. Public access AEDs are relatively easy-to-operate devices for most trained responders that automatically diagnose whether VF (ventricular fibrillation) is present and, if so, urge delivery of defibrillation shocks by a bystander in an attempt to restore normal cardiac rhythm. FIG. 1 is a process flow diagram showing, by way of example, a typical prior art use of a public access AED 12 in an SCA situation. Public access AEDs are designed for repeated use by the general public and require minimal training to operate; users simply follow some combination of voice prompts, text prompts, or both, and diagrammatic instructions to deliver the defibrillation waveforms to SCA victims.

In this example, a victim 18 has suffered suspected cardiac arrest while in the company of a rescuer 19. The terms "victim" and "patient" are used interchangeably and refer to the individual that is receiving emergency care for a possible cardiac arrest. Similarly, the terms "rescuer," "bystander" and "user" are used interchangeably and refer to the individual who is actively providing the emergency care through the use of a public access AED.

When SCA is suspected, often when a victim suddenly loses consciousness and collapses, a rescuer 19 must take immediate action to assist the victim 18, which begins by first locating and obtaining a public use AED 12 (step (1)) and calling 9-1-1. Note that there are two main categories of AEDs, either of which may be found in use as a public use AED. Some AEDs automatically deliver shocks without rescuer action when VF is detected. Most AEDs are semi-automatic and require the rescuer to manually trigger a shock with a button or device control. The portable AEDs carried by emergency medical services (EMS) personnel are generally designed as semi-automatic AEDs that include physiological monitoring tools for both basic and advanced life support, as well as vital signs patient monitoring.

A typical public access AED 12 is located where the general public ordinarily has access kept in some type of protective housing 10, such as a display case, wall cabinet or kiosk. Public access AEDs are designed for long-term reuse and to be available to save multiple victims over their service lifetime, factors that add to unit cost and size, including maintenance obligations and telemetry functionality needed to prevent failures and sustain readiness over time. The public access AED 12 itself is portable and therefore susceptible to being misplaced or stolen; the protective housing 11 helps to keep the public access AED 12 secure and available until needed. Note that, despite being portable, a public access AED kit is bulky and weighs several pounds, which makes carrying a public access-type AED on an everyday basis impractical for most people, even though wider AED availability and use could help save more lives. In addition, both the electrodes and batteries of public access AEDs have expiration dates and must be replaced upon their respective expiry every one to three years. Moreover, these AEDs must undergo periodic operational testing that may require that the defibrillation circuit be energized, resulting in further depleting the battery and prematurely degrading the circuit.

Returning to the steps of AED use in public, once the rescuer 19 locates and obtains an AED, the rescuer must activate the AED 12, which generally entails pressing an "On" button or other controls (step (2)). Conventional public use AEDs 12 are packaged in a large carrying case that contains the AED circuit, including sensing and defibrillation circuit and battery, a pair of adhesive dermal electrode pads 17*a-b* connected by a set of leads 20, and support accessories (not shown), such as gloves and a face shield. Electrode pads are generally about 8-12 cm in length, rectangular, and intended to conform to the human thoracic anatomy.

As some rescuers will be lay bystanders, public use AEDs generally provide visual instructions 14 on assessing the victim's breathing and placement of its electrode pads 17*a-b* on the victim's chest 24 (step (3)). A note should be made however that many public rescuers are in fact medical personnel who take the initiative as a Good Samaritan. Nevertheless, the AED includes a set of necessarily simple controls, typically an "On" button 21 and, if the AED is semi-automatic, a "Shock" button 22 to manually deliver a defibrillation shock by the rescuer, plus a warning indicator 13 that the AED is charged and ready to deliver a defibrillation shock. To activate the public use AED 12, the rescuer 19 simply presses the "On" button 21. The visual instructions 14 are typically supplemented with speaker-generated voice prompts 15, display-generated text prompts 16, in some cases, an electrocardiogram (ECG) 23, or some combination of voice prompts, text prompts and an ECG. The American Heart Association (AHA) and European Resuscitation Counsel (ERC) publishes guidelines outlining a recommended but not mandatory sequence of visual and voice prompts to help rescuers in proper use of AEDs. See, 2010 *American Heart Association Guidelines for CPR and ECC*; Supplement to *Circulation*, Vol. 192, Issue 18 (Nov. 12, 2010). *European Resuscitation Council Guidelines for Resuscitation* 2010, *Resuscitation* Volume 81 (October 2010).

The paddles or electrode pads 17*a-b* must be applied by the rescuer 19 to be in direct contact with the victim's skin. Electrode pads are typically adhesive and, in many AED kits, a razor is included to shave hair off the victim's skin, if needed, on the anatomy where electrode pads are to be placed. To maximize the transit of current through the heart, an anterior-lateral position for electrode pad placement on the victim's chest 24 is preferred. The anterior pad is applied on the right anterior upper chest 24 just below the right clavicle. The lateral pad is applied immediately below and lateral to the left nipple. In female patients, the lateral pad should be applied on the chest wall below and lateral to the left breast, and not over the breast tissue.

With the pads in place, the typical traditionally AED commonly in use will determine if a shockable rhythm is present depending upon the ECG obtained from the pads and instruct the rescuer to deliver a defibrillation shock, if required, to stop VF and allow the heart to reestablish an effective normal rhythm. If the public use AED 12 is semi-automatic, the rescuer 19 will need to manually administer the shock by pressing the "Shock" button 22. At times, traditionally, multiple shocks may be required whereupon rhythm analysis by the AED (step (4)) dictates the timing of recurrent defibrillation shocks. Resuscitation of the victim 18 is unlikely if defibrillation is unsuccessful and/or is delivered too late. Some AEDs provide for escalating energy delivery when a previous shock attempt fails to terminate VF as determined by the ECG. Higher energy delivery may or may not restart the heart, but also more likely to cause temporary damage to cardiac tissue. Further, AEDs with higher shock energies also result in increased weight and cost of the AED minimizing its portability and broad availability and have been well demonstrated to not be required in the early rescue process to terminate ventricular fibrillation.

Moreover, public access AEDs are designed and built to save multiple victims over the service life of the device despite long periods of idle standby storage. These requirements lead to a complex, large, and typically over-engineered design, which also leads to high cost and long-term maintenance obligations. The design and construction of public use AEDs uses large heavy batteries and costly electronic components intended to ensure operability when and if the AED is needed for use. And yet, such costly designs often fail because of their complexity.

As public use AEDs are big and bulky, they are ordinarily only going to be found in a stationary place in a controlled access protective housing, which inherently limits their availability during a SCA emergency and, to a large extent, renders public use AEDs largely ineffective in reducing the number of deaths caused by most SCA deaths that occur in the private settings of the home. Public use-type AEDs are also expensive and seldom found outside of areas where their placement is legally required given the significant economic burden associated with both initial acquisition and ongoing maintenance costs that often exceed the initial price of the AED. Thus, even though most SCAs occur in the home, AEDs are seldom found there, or in countless other random places where people often suffer a SCA, such as in cars and private boats, in parks or trails where people are walking, exercising or enjoying the outdoors, and where people are visiting with friends, and so forth. Despite being portable, the size and weight of a full public use AED kit makes carrying one personally in a backpack or stowed in the glove box of a car impractical.

Conventional AEDs are battery powered and include a charging circuit that uses a step-up transformer to increase battery voltage from low voltage in the range of 6-24 volts (V) to around 1000-6000 V (note that higher voltages are rarely used today), a rectification circuit to convert the high voltage AC energy from the step-up transformer to direct current (DC) energy, and a pulse capacitor to store the energy prior to defibrillation shock delivery. These traditional pulse capacitors are rated to handle high voltage and large sudden discharge currents; as a result, they can be difficult to manufacture and are prone to failure, thereby increasing associated costs. Once this type of legacy pulse capacitor is charged, the AED is ready to deliver a defibrillation shock and the charging circuit switches the energy to the patient, whereby the current is delivered to the victim's chest to complete the circuit. For successful defibrillation, the current delivery waveform must be physiologically appropriate.

Current commercially available AEDs generally employ biphasic truncated exponential (BTE), pulsed biphasic, or rectilinear biphasic waveforms. In contrast to the historical use of monophasic waveforms, properly designed biphasic waveforms are both more effective and require less energy for defibrillation. Accordingly, monophasic waveforms are no longer used. With a biphasic defibrillator, the initial energy level for defibrillation typically begins at 120 J (although it can be less) and can escalate for the second and subsequent defibrillation shocks up to a maximum of 360 J. Energy choice and escalation are waveform and manufacturer-specific and sometimes dependent upon prior intellectual property constraints.

This historical background of the status quo notwithstanding, the life-saving benefits of AEDs can be more efficaciously provided to every person, everywhere and on a 24/7/365 basis through a disposable, single-use AED that is small enough to be truly portable, for instance by fitting in an average-sized pocket. A single use AED, that is, a device that is available to therapeutically treat one instance of SCA, significantly streamlines and simplifies the design requirements of the AED and accordingly makes it possible to house the AED in a small pocketable form factor. Periodic maintenance is not required, as the disposable nature of the pocket AED implies the device will be discarded before needing to undergo maintenance or other testing prior to use on a patient. As well, the failure ratings of the electronic components need only accommodate one use, rather than repeated uses over an extended service life of many years, limiting complexity and improving durability. Similarly, the battery can be smaller and lighter, as battery life will not be depleted by long shelf life and telemetry transmissions related to diagnostic routines and maintenance test cycles. Further, the use of such simplified electronic components and battery technologies lowers cost and allows disposability to be realized. Finally, to encourage being carried by users at all times, the pocket AED is sized comparably to a conventional smartphone, for instance, in the range of 2.25 to 3.5 inches wide, 5.25 to 7 inches long, and 0.25 to 1.5 inches thick, and of similar weight, for example, in the range of 130 to 550 grams.

Figure 2:
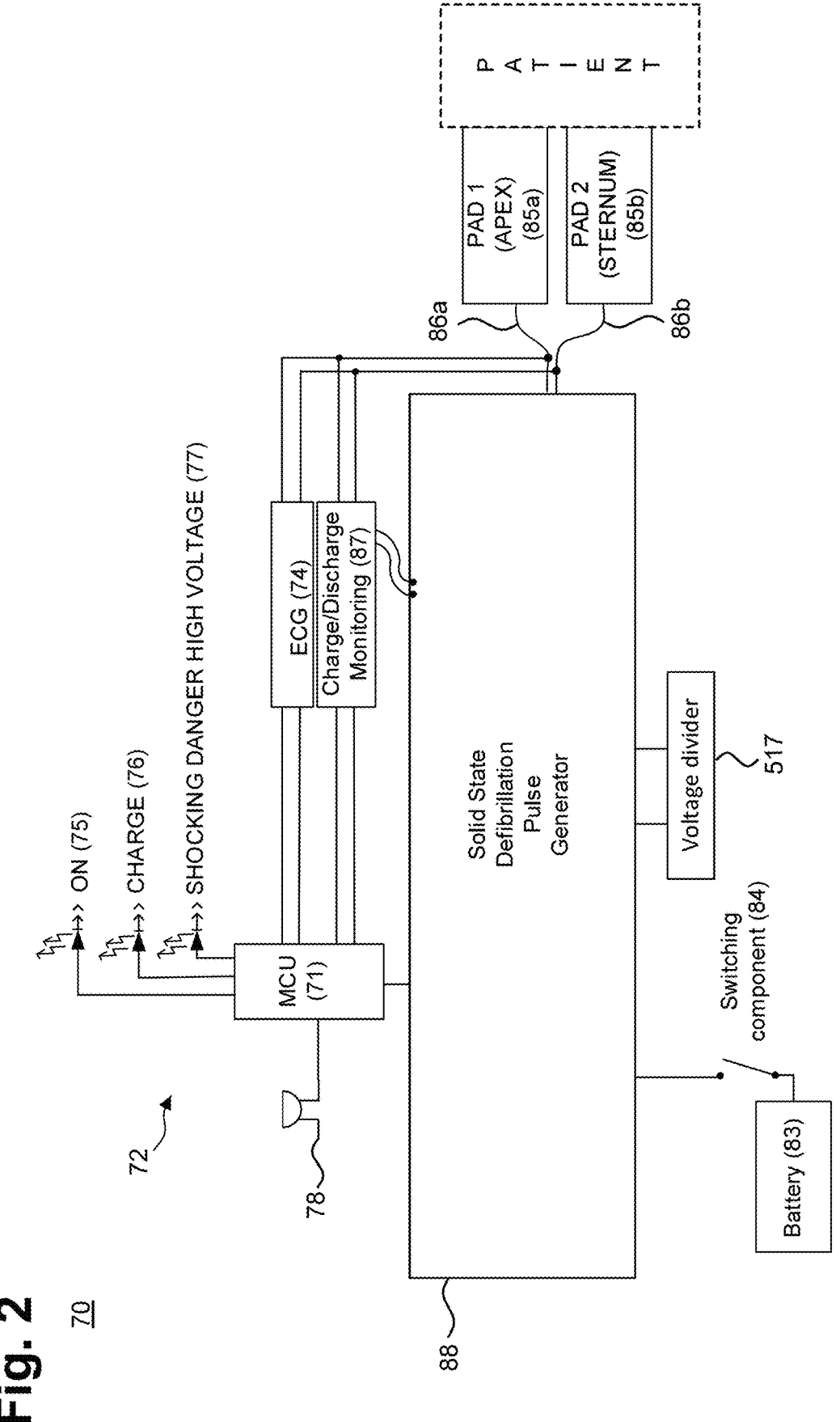
FIG. 2 is a block diagram showing functional components and a user interface for a disposable single use pocketable AED in accordance with one embodiment.

To facilitate the construction of a disposable pocketable AED to fit into a small form factor, various charging configurations are provided. FIG. 2 is a block diagram showing functional components and a user interface 72 for a disposable pocketable AED. For the sake of clarity, only the defibrillation circuit 70 will be discussed in detail.

The defibrillation circuit 70 includes components for providing a basic user interface 72 that includes an "On" switch (not shown), a "Power On Indicator" 75, a charging indicator 76, and optionally, a warning indicator 77 that indicates defibrillation shock delivery readiness with attendant dangers of exposure to high voltage, plus an optional speaker 78 through which audible instructions can be played. The user interface 72 also includes a visual display (not shown) on which text prompts can be displayed. In one embodiment, an AED incorporating the defibrillation circuit 70 can be semi-automatic and require the rescuer to manually trigger a shock by actuating the charging indicator 76; in a further embodiment, an AED incorporating the defibrillation circuit 70 employs a circuit to automatically deliver the defibrillation shock to the victim without user action once the pulse generation circuit 88 is ready, that is, the pulse capacitor 81b is charged by a high voltage charger circuit 81a and is ready to provide power to a solid-state defibrillation waveform therapy generator 406, and after the user has been warned to avoid any direct physical contact with the patient during shock delivery. The defibrillation circuit 70 includes a battery 83 powering the rest of the circuitry via a switching component 84, which can be a switch, as described in U.S. patent application Ser. No. 18/401,199, filed Dec. 29, 2023, active power control circuit or switched relay. The defibrillation circuit 70 is controlled by a microcontroller unit (MCU) 71 or system-on-chip controller (SoC) (not shown) that is programmable, which allows updated controller firmware to be downloaded from an external programmer into a persistent memory store. Sensing circuit 87 is connected in line with the inputs and outputs of a discharge and polarity control circuit 88. The sensing circuit (74) and MCU (71) determines whether a shockable rhythm is present. The defibrillation energy that is received from the pulse capacitor 81b as an input to the discharge and polarity control circuit 88 and the defibrillation waveform or "pulse" that is output. ECG front end circuit 74 evaluates heart rhythm for the MCU 71. The ECG front end circuit 74 taps off the leads 86a-b of the pair of electrode pads 85a-b to sense cardiac signals, as does the sensing circuit 87 to monitor the shock delivery process. A shockable rhythm is detected by the ECG circuit (74) in conjunction with an algorithm running on the MCU (71) such as a conventional VF detection algorithms to detect the presence of a shockable rhythm, such as published by A.

Fan, et al., Shockable Rhythm Detection Algorithms for Electrocardiograph Rhythm in Automated Defibrillators, AASRI Conf. on Comp. Intel. and Bioinfor. pp. 21-26 (2012). The ECG front end circuit 74 is implemented through a conventional ECG front end such as the ADS1x9xECG-FE family of integrated analog front-end ECG circuits, available from Texas Instruments, Dallas, TX. Other types and configurations of sensing and ECG front end circuitries are possible.

When a shockable rhythm is detected, based on inputs from the ECG front end circuit 74, the MCU 71 determines the ideal parameters of a defibrillation waveform in terms of energy, voltage, and pulse width; the defibrillation waveform is algorithmically selected based on the nature of the shockable rhythm and patient impedance to be medically appropriate for restoring normal cardiac rhythm. Up to a maximum of three shocks may be needed if the victim fails to be resuscitated, after which further shocks are generally futile, but may be optionally provided.

In response to the ECG circuit 74 determining that a shockable rhythm is still present after initial shock delivery, that is, defibrillation failed to establish normal cardiac rhythm, the MCU 71 may be programmed to repeat the delivery of the defibrillation pulse or, if appropriate, revise the parameters of the defibrillation waveforms for the subsequent pulses. In this situation, subsequent defibrillation shocks may need to be escalated for the second and subsequent defibrillation shocks, generally up to a maximum of 360 J. In a further embodiment, parameters consisting of one or more of energy, voltage and pulse width are adjusted by the MCU 71 in real time, as further discussed infra with reference to FIG. 4.

Figure 3:
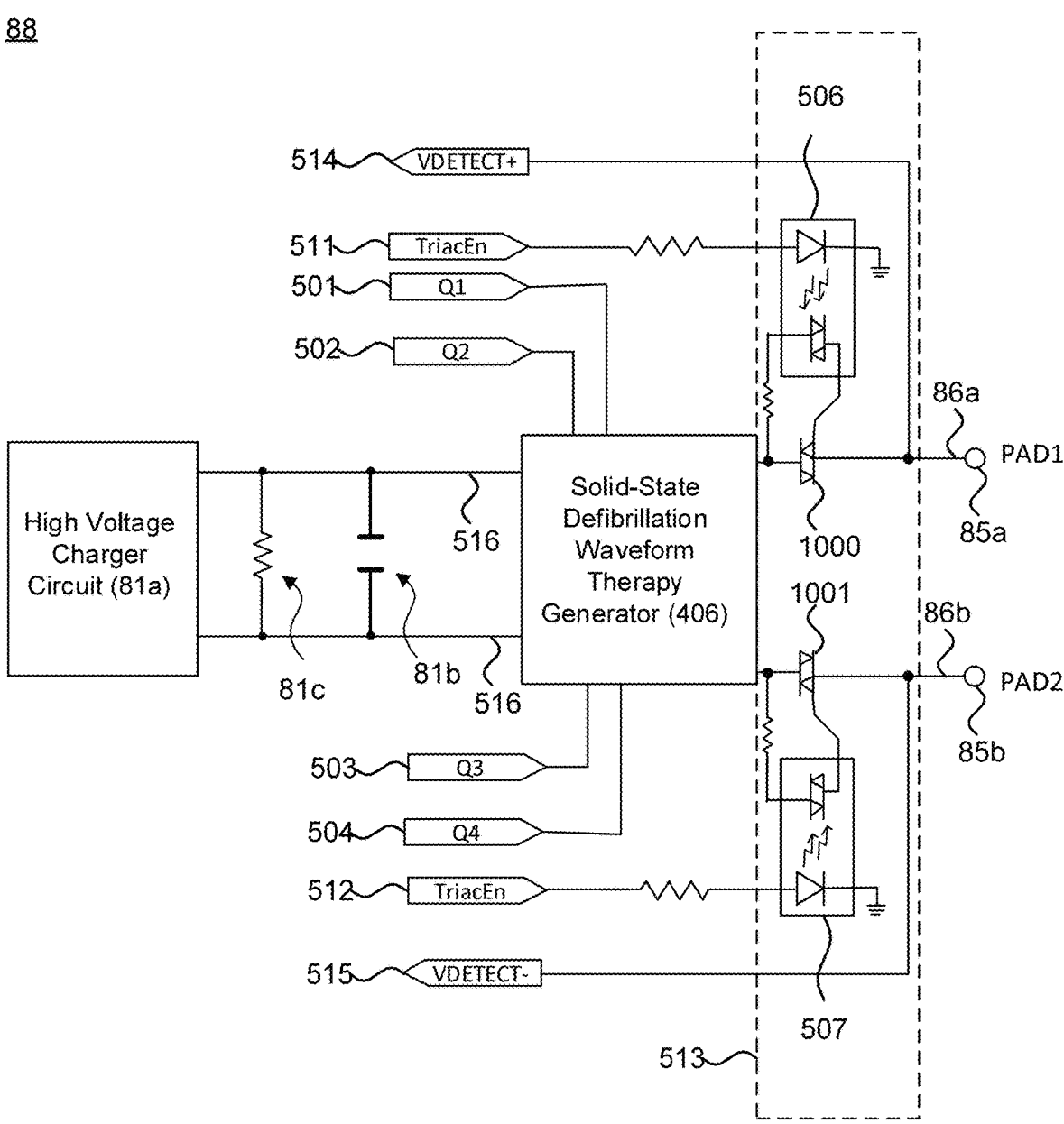
FIG. 3 is a diagram showing of the pulse generation (discharge circuit) i of FIG. 2, including patient protection circuitry, in accordance with one embodiment.

Defibrillation energy is generated and stored as part of a pulse generation circuit 88 (also referred to as a waveform generator 88) that include patient protection circuitry providing additional means for keeping the patient safe from accidental discharges. FIG. 3 is a diagram showing pulse generation circuit of FIG. 2, including patient protection circuitry, in accordance with one embodiment. The pulse generation circuit 88 includes a high voltage charger circuit 81a, including an optional bleeder resistor safety component 81c and a high-voltage defibrillation capacitor 81b with energy that is stored for delivery as a defibrillation shock. The bleeder resistor 81c is positioned across the defibrillation capacitor 81b allowing fail-safe self-discharge.

The pulse capacitor 81b in turn delivers the energy to a solid-state defibrillation therapy generator circuit 406 that generates the defibrillation waveform under the control of the MCU 71. The solid-state defibrillation waveform therapy generator circuit 406 generates the defibrillation shock provided to the patient through the pads 85a, 85b (also referred to as electrodes 85a, 85b). In particular, the solid-state defibrillation waveform therapy generator circuit 406 includes multiple solid-state switching elements (not shown) whose output, when combined, determines the polarity of the defibrillation waveforms delivering the shock, as described in U.S. patent application Ser. No. 18/806,588, filed Aug. 15, 2024, and U.S. patent application Ser. No. 18/806,524, filed Aug. 15, 2024, the entire disclosures of which are incorporated by reference. In one embodiment, the solid-state defibrillation waveform therapy generator 406 can be in the form of an H-Bridge while the solid-state switching elements can be one or more of a field-effect transistors (FETs), and one or more silicon-controlled rectifiers (SCRs), triode for alternating current (TRIAC), a bipolar junction transistors (BJTs) or a combination of one or more of the different types of element. The FETs can in turn can include one or more insulated-gate bipolar transistors (IGBTs) and one or more Silicon Carbide FETs, though other types of FETs are also possible. Still other types of elements are possible. In one embodiment, the solid-stat switching elements can be MMIX4B22N30 High Voltage, High Gain BIMOSFET™ Monolithic Bipolar MOS Transistor sold by IXYS Corporation of Milpitas, California, though other types of the solid-state defibrillation waveform therapy generator 406 are possible. The solid-state defibrillation waveform therapy generator circuit 406 is interfaced to the MCU 71 via four pins 501-504 and controls the generation of the defibrillation waveforms by the circuit via the four pins 501-504 (with each pin being interfaced to one of the solid-state switching elements of the circuit 406), though in a further embodiment, pins could be paired together for simplified operation.

The solid-state defibrillation waveform therapy generator circuit 406 is also interfaced to one or more triodes for alternating current (TRIACs) 1000, 1001 that provide an additional means of protection to protect the patient from accidental discharge. The TRIACS 1000, 1001 can be identical, though in a further embodiment, the TRIACs 1000, 1001 can differ from each other. Each TRIAC 1000, 1001 is positioned between the circuit 406 and one of leads 86a, 86b leading to one the pads 85a, 85b (and thus through which defibrillation waveforms are delivered). As the voltage of defibrillation waveforms is generally at least 1850 volts while commercially available TRIACs can handle up to 1800 volts, the pulse generation circuit 88 includes at least two TRIACs 1000, 1001, as can be seen with reference to FIG. 3. More than two TRIACs 1000, 1001 can be included as part of the pulse generation circuit. When two or more TRIACs 1000, 1001 are included as part of the pulse generation circuit 88, the TRIACs 1000, 1001 can be positioned in a series when the TRIACs are positioned between the circuit 406 and the same one of the leads 86a, 86b. Alternatively, or in addition to multiple TRIACs 1000, 1001 being positioned in a series, as can be seen from FIG. 3, TRIACs 1000, 1001 or groups of TRIACS 1000, 1001 can positioned between the circuit 406 and both of the leads 86a, 86b. Further, if a single TRIAC 1000, 1001 (either currently existing custom-made TRIAC 1000, 1001, or a TRIAC 1000, 1001 that becomes commercially available in the future) can handle the 1850 volts, the pulse generation circle 88 can include only a single TRIAC 1000, 1001. In one embodiment, the TRIACs 1000, 1001 can be BTA408X-1000COT sold by WeEn Semiconductors Co., Ltd headquartered in Shanghai, China, though in a further embodiment, other types of TRIACs 1000, 1001 can also be used.

Each of the TRIACs 1000, 1001 is controlled by the MCU 71 via one of the pins 511, 512. Under the control of the MCU 71, each of the TRIACs 1000, 1001 can switch between an enabled configuration (also referred to as "an enabled state" or "conductive state") and a non-enabled configuration (also referred to as "non-enabled state" or "isolated state"). In the conductive state, the TRIACs 1000, 1001 allow the defibrillation waveforms generated by the circuit 406 to reach the patient through the pads 85a, 85b. In the isolated state the TRIACs 1000, 1001 prevent the defibrillation waveforms from reaching the patient through the pads 85a, 85b. The default state of the TRIACs 1000, 1001 is the isolated state and the MCU 71 switches the TRIACs 1000, 1001 into the conductive state only when delivery of the defibrillation shock becomes necessary. Once the requisite defibrillation waveforms are delivered, the MCU 71 can return the TRIACs 1000, 1001 to the isolated state.

In one embodiment, the TRIACs 1000, 1001 are driven by TRIAC drivers 506, 507 that are directly interfaced to the pins 511, 512, with the driving causing the switching of the TRIACs between the states. In one embodiment, the TRIAC drivers 506, 507 can be optically coupled with the TRIACs 1000, 1001, though in a further embodiment, other kinds of couplings are also possible. In one embodiment, the TRIAC drivers 506, 507 can be MOC3021 TRIAC Driver Optocouplers sold by Semiconductor Components Industries, LLC dba ONSEMI of Scottsdale Arizona, though in a further embodiment, other TRIAC drivers are also possible.

In a further embodiment, power supplied to the gates of the TRIAC (1000, 1001), is generated by a bias generator, optionally connected to the bias voltages internally generated to the Solid-State Defibrillation Waveform Therapy Generator (406).

The TRIACS 1000, 1001 and the TRIAC drivers 506, 507 form part of a safety circuit 513 protecting the patient. The safety circuit 513 can include other components or be limited to the TRIACs 1000, 1001 and the TRIAC drivers. In a further embodiment, the TRIACs 1000, 1001 could be replaced in the safety circuit 513 by an array of one or more of one or more IGBTs and at least one of one or more bipolar junction transistor (BJTs) or one or more metal-oxide-semiconductor field-effect transistor (MOSFETs).

As the passage of time can cause degradation of the TRIACs and other components of the safety circuit, the MCU 71 monitors and analyses the performance of the safety circuit 513 to ensure the safety circuit's continued integrity. If the performance of the safety circuit falls below a predefined threshold, the MCU 71 takes an action, such as disabling the charging of the solid-state defibrillation waveform therapy generator 406 or causing a discharge of the pulse capacitor 81b, though other actions are also possible. The monitoring is performed using a voltage monitor (not shown) interfaced the microcontroller 71 to detect leakage currents. The monitoring is done via pins 514, 515 connected to the leads 86a, 86b between the TRIACs 1000, 1001 and the pads 85a, 85b. If the voltage monitor detects via the pins 514, 515 voltage exceeding a predefined threshold (which can be close to zero volts or a different number of volts) when the TRIACs 1000, 1001 are in the isolated state (thus amounting to a current leakage (also referred to as a "current leak" below)), then the integrity of the safety circuit is determined to be comprised. The voltage monitor can include a voltage divider 517 (with one side of the voltage divider being interfaced to one of the pins 514, 515 and another side of the voltage divider being interfaced to another one of the pins 514, 515) as well as other circuitry necessary for the voltage monitoring, such as a comparator, an analog-to-digital converter (ADC), a processing element (such as a microcontroller), though still other components of the voltage monitor are also possible. The voltage monitor can further detect current leaks from other components of the pulse generation circuit 88. For the example, the voltage monitor can be interfaced to leads 516 between the high voltage charger circuit 81a and the solid-state defibrillation waveform therapy generator 406 and detect current leaks when the charger circuit 81a is not supposed to be under bias, with the MCU 71 taking an action (such as disabling the charging of the solid-state defibrillation waveform therapy generator 406 or causing a discharge of the pulse capacitor 81b, though actions are also possible) based on the current leaks detected on the leads 516. Still other places of the circuit 88 where the voltage could be analyzed by the MCU 71 through the voltage monitor and an action taken by the MCU 71 based on that monitoring are also possible.

In addition to monitoring for leakage currents, the MCU 71 provides an additional layer of safety to prevent unintended shocking of the patient. In particular, the MCU 71 controls when different portions of the circuit 88 are powered up. Thus, the high voltage charger circuit 81a, the solid-state waveform generator 406, and the safety circuit 513 remain unpowered until the MCU 71 receives the command for delivering the defibrillation shock and provides power to these elements of the circuit 88. The lack of bias decreases the damage to the elements caused through dielectric wear thus increasing the reliability and prolonging the life of the circuit 88.

Figure 4:
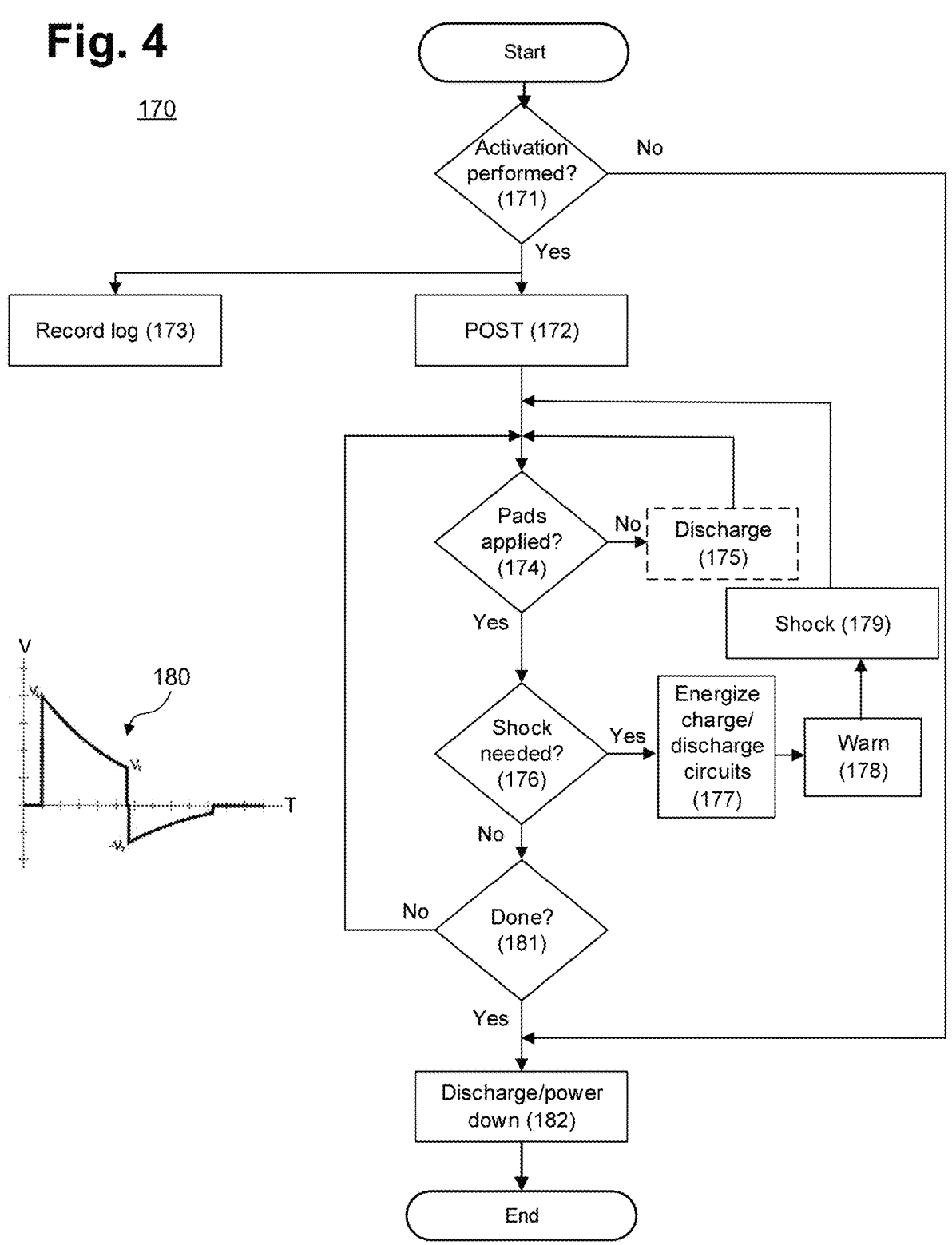
FIG. 4 is a flow chart showing a method for operating a disposable pocketable AED in accordance with one embodiment.

A disposable pocketable AED using the pulse generation circuit 88 is intended to be available at all times and easy to use with little to no training required. FIG. 4 is a flow chart showing a method 170 for operating a disposable pocketable AED in accordance with one embodiment. To start, the AED is activated (step 171) by the user pressing the "On" switch, removing the outer wrapping, opening the case or similar control, after which the AED executes a power-on self-test (POST) (step 172). As part of the power-on self-test, the MCU 71 can determine presence or absence of leakage current from the safety circuit 513 or another components of the circuit 88 using the voltage monitor as described above. The checking for leakage current could also be done at other points of the method 170, such as after delivery of a second one of multiple defibrillation shocks, with the method 170 being aborted if voltage leaks are detected and other actions described above being taken.

Following successful POST [Power On Self Test](step 172), both a record of the AED's activation is made in an onboard log (step 173). The state of the electrode pads is determined (step 174). If the pads are not correctly applied (step 174), such as because the user of the AED has removed the pads from the victim 18, if there is any energy previously generated for delivery of the shock, the energy is dissipated, such as by activating the waveform generator 406 in the transconductance range under the control of the MCU 71 (step 175), which either ends the method 170 or returns the method to step 174, depending on the actions of the user.

If the pads are correctly applied, the AED determines whether a shockable rhythm is present (step 176). Provided a shockable rhythm is sensed (step 171), MCU 71 provides power to the circuit 88 (including the high voltage charger circuit 81a, pulse capacitor 81b, and the safety circuit 513) and turns on the TRIACs 1000, 1001 into the conductive state (step 177). The AED issues a warning to the user (step 178) and a defibrillation shock is delivered (step 179). The defibrillation shock is delivered as a high voltage therapeutic waveform 180, preferably as a biphasic waveform, such as a biphasic truncated exponential (BTE), pulsed biphasic, and rectilinear biphasic waveform, modified biphasic, arbitrary or, alternatively, as a monophasic waveform. Other defibrillation waveforms are possible. Once the shock has been delivered, the device determines whether a normal rhythm has been restored and, if so, the methodology is done (step 181) and the AED will discharge any remaining energy stored in the pulse capacitor 81b, reverse the TRIACs 1000, 1001 to the isolated state, and power down (step 182) after 15 minutes of a non-VF rhythm (182), ending the method 170. In some cases, several defibrillation shocks are required and the AED delivers biphasic defibrillation shocks, where the initial energy level for defibrillation begins at 120 J and either repeats or escalates for the second and subsequent defibrillation shocks up to a maximum of 360 J. In the use of escalation, the defibrillation energy is automatically adjusted by the AED with each subsequent defibrillation shock. In a further embodiment, based on the findings of a detection algorithm performed by the MCU 71 revealing success or failure of preceding defibrillation shocks the polarity of the defibrillation shock is reversed on the third shock (or any subsequent shock following the first shock) should no restoration of a non-shockable rhythm occur. In a further embodiment, the AED can automatically limit the number of shock re-attempts permitted, as after three defibrillation shocks, resuscitation of the victim 18 becomes unlikely.

In a further embodiment, as part of the process of delivering the defibrillation shock (step 179), the AED measures patient impedance during application of the defibrillation shock through the sensing circuit and adjusts one or more of the energy, voltage, and pulse width of the defibrillation waveform 180 in real time to generate optimal defibrillation therapy, where the x-axis represents time (T) and the y-axis represents voltage (V). Knowledge of patient impedance is crucial in a traditional design, which is used to determine the energy required to pre-charge the high-voltage pulse capacitor 81b to an appropriate level and to aid in realizing an appropriate energy deliver waveform. In practice, patient impedance changes during the shock, so conventional impedance-based pre-charge circuits have limited usefulness in achieving effective defibrillation. For instance, the average impedance of a ten-year-old child can be around 20 Ohms, whereas a 200-pound, middle-aged male has an can have an impedance of about 75 Ohms. For both individuals, a waveform of 10 msec is likely necessary for effective defibrillation but their defibrillation energy and pre-charge parameters are different. Moreover, impedance on the skin's surface typically decreases as defibrillation therapy progresses. Optionally the MCU 71 (shown in FIG. 2) interfaces to the sensing circuit to continually measure impedance in real time and adjusts parameters in the high voltage energy delivery module 79, voltage and pulse width (duration). Other implementations are possible.

For instance, an exemplary biphasic waveform is defined with an asymmetrical 65% tilt from a leading-edge voltage $V_L$ and trailing edge voltage $V_T/-V_T$ with a polarity reversal halfway through the waveform. Patient impedance can affect the duration of the waveform where increased impedance means longer pulse width, lower voltage, or less energy to the heart, and decreased impedance means shorter pulse width, higher voltage, or more energy to the heart (unless patient impedance changes after the impedance is sensed). The most efficacious way to ensure correct energy delivery is to monitor and adjust the therapy in real time. One or more of these parameters can be adjusted by the MCU in real time to alter the amount of primary of the shock to reflect the ideal target therapy represented by the biphasic waveform.

FIG. 5 is a front view showing a disposable single use pocketable AED with dual free-floating electrodes in accordance with one embodiment. The AED 230 combines a highly portable form factor with the charging circuit 88 that deliver defibrillating energy out of only modest lightweight battery capacity. Such a pocket-sized AED can be made readily available not just in the home, but anytime and anywhere that a would-be rescuer happens to be. The AED 230 advantageously uses the charging circuit 88, as discussed supra with reference to FIG. 3 et seq., to generate the bias voltage driving the waveform generator 406. This innovation allows the circuit to be powered with a low cost and lightweight battery and the high voltage charger circuit 81a and pulse capacitor 81b to be down-rated from the high capacitance levels utilized in conventional designs, all of which significantly decreases cost and size, thereby making single-use and device disposability possible.

The AED 230 is housed in a small lightweight housing 231, about the size and weight of a mobile telephone, that is, in the range of 2.25 to 3.5 inches wide, 5.25 to 7 inches tall, and 0.25 to 1.0 inches deep and a weight in the range of 130 to 550 grams. Other sizes and form factors are possible. The pair of free-floating electrodes 232a-b are connected to the housing 231 by a pair of flexible leads 233a-b. The charging circuit 88 as described above is interfaced to the electrodes 232a, b. Each electrode 232a-b is coated with an adhesive hydrogel that ensures proper contact with the victim's skin. The electrodes 232a-b are for a single-use only. The front of the AED 230 has a user interface 234 designed to optimize user understanding that includes a set of visual instructions 237. Optionally, the AED 230 can be equipped with a speaker (not shown) to generate voice prompts.

The AED 230 includes a streamlined and simple user interface that facilitates understanding and proper use during an emergency by lay people. Power is controlled by a simple "On" switch 235 that is automatically activated upon use and the status of the AED 230 is intuitively provided by a visual indicator 236 that changes color depending upon the state of the AED, for instance, through a display of "red," "yellow" and "green" to respectively indicate device activated but not attached to the patient, device attached and pulse capacitor 81b charging, and a ready-to-shock condition. Other colors, forms and types of indicators are possible. Other information, such as impedance and voltage, vital signs, thoracic activity, actigraphy, motion or environmental information, as well as other information can similarly be provided to the user interface or recorded for later analysis. In a further embodiment, the AED 230 includes mobile communications capabilities by which to automatically summon medical assistance, generally by calling 9-1-1 or the equivalent in most localities, upon the sensing of a shockable rhythm. The mobile communications capabilities integrated into the AED 230 by including appropriate circuits and components or through a special features module providing the mobile communications capabilities to the AED. The AED could also receive mobile communications capabilities through a wireless interface, such as WiFi or Bluetooth, over which the AED can communicate to a mobile phone or wide area network, such as the Internet, and relay a 9-1-1 call. Alternatively, a mobile phone or device could be supplemented with the features of the AED 230.

FIG. 6 is a cut-away view showing block component groups contained within the disposable single use pocketable AED 230 of FIG. 10. The AED's circuit is provided on a printed circuit board (PCB) 240 contained within the housing 231, which also contains a low-cost, high-energy density battery 238 (optionally, a primary cell) and a pulse capacitor 239.

FIG. 7 is a side view showing the disposable single use pocketable AED 230 of FIG. 5 with the housing and dual free-floating electrodes stowed in a carrying case 242. The AED 230 is intended to be easily carried in a pocket and could be carried in a purse, backpack, glovebox, golf bags, and so forth, so as to enable the AED 230 to be conveniently on-hand in case of an SCA situation in the same manner that most people have their mobile phone on-hand.

FIG. 8 is a side view showing the disposable single use pocketable AED 230 of FIG. 5 with the housing and dual free-floating electrodes partially deployed from the carrying case 242. The pair of free-floating electrodes 232a-b share a similar front profile with the housing 231. The housing 231 and electrodes 232*a-b* slide out of the carrying case 242 when being deployed.

FIG. 9 is a back view showing the cable management system 241 of the disposable single use pocketable AED 230 of FIG. 5. A cable management system 241 is used to store the leads 232*a-b* inside of the housing 231, where the leads are internally retracted by the smart cable management system 241 until needed.

One of the dual free-floating leads 232*a-b* can be eliminated by providing an electrode pad surface on the AED's housing. FIG. 10 is a front view showing a disposable single use pocketable AED 250 with a single free-floating electrode 252 in accordance with one embodiment. As before, the AED 250 is housed in a small lightweight housing 251, but only one free-floating electrode 252 is connected to the housing 31 by a single flexible lead 253.

FIG. 11 is a rear view showing the integrated electrode 258 of the disposable single use pocketable AED 250 of FIG. 10. An integrated electrode pad 258 is provided on a rear-facing surface of the housing 251. A planar laminated high energy pulse transformer is incorporated into each electrode 252, 258, as further discussed infra with reference to FIG. 19. Both the single free-floating electrode 252 and integrated electrode 258 are coated with an adhesive conductive hydrogel that ensures proper contact with the victim's skin. The front of the AED 250 similarly has a user interface 254 designed to optimize user understanding that includes a set of visual instructions 257. Optionally, the AED 250 can be equipped with a speaker (not shown) to generate voice prompts. Power is again controlled by an "On" switch or optionally an activation circuit 255 and the status of the AED 250 is provided by a visual indicator 256. The AED's circuit is provided on a PCB (not shown) contained within the housing 251, which also contains a low-cost, high-energy density battery (not shown) and pulse capacitor (not shown).

FIG. 12 is a side view showing the disposable single use pocketable AED 250 of FIG. 5 with the housing 251 and single free-floating electrode 252 stowed in a carrying case. The single free-floating electrode 252 shares a similar profile with the housing 251.

FIG. 13 is a side view showing the disposable single use pocketable AED of FIG. 5 with the housing and single free-floating electrodes partially deployed from the carrying case. The housing 251 and electrode 252 slide out of the carrying case 260 when being deployed. A smart cable management system (not shown) is also used to store the single lead 253 inside of the housing 251, where the lead is internally retracted by a cable management system until needed.

FIG. 14 is a top view diagram showing an electrode pad assembly 271 for use in the disposable single use pocketable AEDs 230, 250 of FIGS. 5 and 10. Each electrode contains an embedded planar laminated high energy pulse transformer. This type of transformer exhibits high power density by functioning at high switching frequencies, while packaged in a low profile with larger surface area, thereby preventing overheating. In each electrode assembly 271, a primary winding 272 and a secondary winding 273 are laminated together into a planar transformer 270 with a jumper that is soldered, welded, crimped, or otherwise electrically conducted together.

The circuits described herein provides the basis for external defibrillators that are easy to carry, low cost and lightweight, while delivering a high-voltage, high-energy biphasic shock suitable for cardiac defibrillation and victim resuscitation. External defibrillators utilizing this circuit can help to facilitate the widespread adoption of the portable defibrillation technology and thereby meaningfully help to decrease the number of deaths from sudden cardiac arrest. Moreover, such circuits could also aid in reducing size and cost of implantable defibrillators.

In a further embodiment, the circuits described herein, including the circuit 88 described with reference to FIGS. 3, could be incorporated into an implantable cardioverter defibrillator (ICD). In a still further embodiment, the circuits could be incorporated into a wearable external defibrillator.

The descriptions of the AED and circuits above can be combined with the features described in the following commonly-owned patent documents: U.S. Pat. No. 11,794,026, issued Oct. 24, 2023; U.S. Pat. No. 12,168,137, issued Dec. 17, 2024; U.S. Pat. No. 12,220,592, issued Feb. 11, 2025; and U.S. Patent Application entitled "Circuit For Defibrillation Waveform Generation," Ser. No. 18/806,588, filed Aug. 15, 2024; and U.S. patent application Ser. No. 18/982,957, filed Dec. 16, 2024. The entire disclosures of all of these five patent documents is hereby incorporated by reference.

While the invention has been particularly shown and described as referenced to the embodiments thereof, those skilled in the art will understand that the foregoing and other changes in form and detail may be made therein without departing from the spirit and scope of the invention.

What is claimed is:

1. A defibrillator with solid state patient protection circuitry, comprising:

a therapeutic defibrillation waveform generator configured to generate one or more therapeutic defibrillation waveforms for delivery to a patient via a pair of leads, each of the leads directly connected to one of two pads configured to directly contact the patient during the delivery of the therapeutic defibrillation waveforms;

patient protection circuitry comprising a safety circuit comprising one or more triodes for alternating current (TRIACs) that are separate from the therapeutic waveform generator and that are positioned in series directly between the therapeutic defibrillation waveform generator and at least one of the leads, each of the TRIACs configured to switch between a conductive and an isolated state, wherein the TRIACs prevent the therapeutic defibrillation waveforms from reaching the patient in the isolated state and allow the defibrillation waveforms to reach the patient in the conductive state; and a control element configured to control the therapeutic defibrillation waveform generation by the therapeutic defibrillation waveform generator and the switching of the TRIACs between the conductive state and the isolated state, wherein the control element is further configured to analyze a performance of the safety circuit and to take an action based on the analysis.

2. A defibrillator in accordance to claim 1, wherein all of the TRIACs are positioned in series between the therapeutic defibrillation waveform generator and one of the leads.

3. A defibrillator in accordance to claim 1, wherein at least one of the TRIACs is positioned between the therapeutic defibrillation waveform generator and each of the leads.

4. A defibrillator in accordance to claim 1, further comprising:

a voltage monitor interfaced to the control element and configured to detect leakage current from the safety circuit, wherein the analysis is based on the detected levels of leakage current.

5. A defibrillator in accordance to claim 4, wherein the voltage monitor comprises a voltage divider and detection circuitry.

6. A defibrillator in accordance to claim 4, wherein the leakage currents are isolated from the patient on electrical connections between the safety circuit and the therapeutic defibrillation waveform generator.

7. A defibrillator in accordance to claim 4, further comprising:

a charging circuit configured to charge the therapeutic defibrillation waveform generator via a defibrillation capacitor, wherein the voltage monitor is further configured to detect one or more further leakage current from at least one of the charging circuits and the therapeutic defibrillation waveform generator and to take the action based on the detection of at least one of the further current leaks.

8. A defibrillator in accordance to claim 7, further comprising:

the control element configured to receive a command to deliver one or more of the therapeutic defibrillation waveforms to the patient and to activate the charging circuit, the therapeutic defibrillation waveform generator, and disable the safety circuit upon receiving the command, wherein the charging circuit, the therapeutic defibrillation waveform generator, and the safety circuit are not under power until activated by the control element that activates a high voltage generator.

9. A defibrillator in accordance to claim 1, wherein the action comprises disabling charging of the therapeutic defibrillation waveform generator and causing a self-discharge of the therapeutic defibrillation waveform generator energy storage element.

10. A defibrillator in accordance to claim 1, further comprising:

one or more TRIAC drivers, each of the TRIAC drivers interfaced to one of the TRIACs and configured to drive that TRIAC under a control of the control element, wherein the driving by the TRIAC drivers causes the TRIACs to switch from the isolated state to the conductive state.

11. A defibrillator in accordance to claim 1, wherein the therapeutic defibrillation waveform generator is an H-Bridge configuration.

12. A defibrillator with patient protection circuitry, comprising:

a therapeutic defibrillation waveform generator configured to generate one or more therapeutic defibrillation waveforms for delivery to a patient via a pair of leads, each of the leads directly connected to one of two pads configured to directly contact the patient during the delivery of the therapeutic defibrillation waveforms;

a charging circuit configured to charge the therapeutic defibrillation waveform generator via a defibrillation capacitor;

patient protection circuitry comprising one or more triodes for alternating current (TRIACs) separate from the therapeutic waveform generator and positioned directly between the therapeutic defibrillation waveform generator and at least one of the leads, each of the TRIACs configured to switch between a conductive state and an isolated state, wherein the TRIACs prevent the therapeutic defibrillation waveforms from reaching the patient in the isolated state and allow the therapeutic defibrillation waveforms to reach the patient in the conductive state; and a microcontroller control element configured to deliver one or more of the therapeutic defibrillation waveforms and to cause shifting of the TRIACs from the isolated state to the conductive state and activation of the charging circuit and the therapeutic defibrillation waveform generator, wherein the charging circuit and the therapeutic defibrillation waveform generator are not under bias until the activation of the charging circuit.

13. A defibrillator in accordance to claim 12, wherein all of the TRIACs are positioned in a series between the therapeutic defibrillation waveform generator and one of the leads.

14. A defibrillator in accordance to claim 12, wherein at least one of the TRIACs is positioned between the therapeutic defibrillation waveform generator and each of the leads.

15. A defibrillator in accordance to claim 12, wherein the patient protection circuitry comprises a safety circuit comprising the TRIACs and the microcontroller control element is further configured to detect one or more leakage currents in one or more of the safety circuit, the charging circuit, and the therapeutic defibrillation waveform generator, and to take an action based on the detection of at least one of the leakage currents.

16. A defibrillator in accordance to claim 15, further comprising:

a voltage monitor interfaced to the microcontroller control element and configured to detect the one or more leakage currents from one or more of the safety circuit, the charging circuit, and the therapeutic defibrillation waveform generator and to report the detected leakage to the microcontroller control element.

17. A defibrillator in accordance to claim 15, wherein the action comprises disabling charging of the therapeutic defibrillation waveform generator and causing a self-discharge of the therapeutic defibrillation waveform generator.

18. A defibrillator in accordance to claim 15, further comprising:

at least two TRIAC drivers comprised in the safety circuit, each of the TRIAC drivers interfaced to one of the TRIACs and configured to drive that TRIAC under a control of the microcontroller control element, wherein the driving by the TRIAC drivers causes the TRIACs to switch from the isolated state to the conductive state.

\* \* \* \* \*